US011207449B2

(12) United States Patent
Petrucci

(10) Patent No.: US 11,207,449 B2
(45) Date of Patent: *Dec. 28, 2021

(54) METHODS AND MATERIALS FOR TREATING BLOOD VESSELS

(71) Applicant: Gary M. Petrucci, Long Lake, MN (US)

(72) Inventor: Gary M. Petrucci, Long Lake, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/677,317

(22) Filed: Nov. 7, 2019

(65) Prior Publication Data

US 2020/0069849 A1    Mar. 5, 2020

Related U.S. Application Data

(63) Continuation of application No. 15/708,406, filed on Sep. 19, 2017, now Pat. No. 10,478,531.

(60) Provisional application No. 62/523,366, filed on Jun. 22, 2017.

(51) Int. Cl.

| A61L 31/16 | (2006.01) |
| A61F 2/07 | (2013.01) |
| A61L 31/08 | (2006.01) |
| A61M 25/10 | (2013.01) |
| A61L 29/16 | (2006.01) |
| A61L 29/08 | (2006.01) |
| A61L 31/14 | (2006.01) |
| A61L 27/38 | (2006.01) |

(52) U.S. Cl.
CPC ............... *A61L 31/16* (2013.01); *A61F 2/07* (2013.01); *A61L 29/085* (2013.01); *A61L 29/16* (2013.01); *A61L 31/08* (2013.01); *A61M 25/104* (2013.01); *A61L 27/3804* (2013.01); *A61L 31/148* (2013.01); *A61L 2300/416* (2013.01); *A61M 2025/105* (2013.01)

(58) Field of Classification Search
CPC .................... A61L 31/16; A61F 2/07
See application file for complete search history.

(56) References Cited

U.S. PATENT DOCUMENTS

| 4,828,844 | A | 5/1989 | Rontgen-Odenthal et al. |
| 5,049,389 | A | 9/1991 | Radhakrishnan |
| 5,131,907 | A | 7/1992 | Williams et al. |
| 5,524,462 | A | 6/1996 | Loughlin |
| 5,656,498 | A | 8/1997 | Iijima et al. |
| 5,674,192 | A | 10/1997 | Sahatjian et al. |
| 5,725,519 | A * | 3/1998 | Penner ................... A61F 2/958 606/1 |
| 6,293,959 | B1 * | 9/2001 | Miller ................... A61F 2/958 604/103.07 |
| 7,524,489 | B2 | 4/2009 | Messina et al. |
| 7,682,803 | B2 | 3/2010 | Paludan et al. |
| 8,323,701 | B2 | 12/2012 | Daniel et al. |
| 8,357,403 | B2 | 1/2013 | Daniel et al. |
| 8,372,437 | B2 | 2/2013 | Daniel |
| 8,372,438 | B2 | 2/2013 | Daniel et al. |
| 8,372,439 | B2 | 2/2013 | Daniel et al. |
| 8,409,626 | B2 | 4/2013 | Daniel et al. |
| 8,460,715 | B2 | 6/2013 | Daniel |
| 8,460,716 | B2 | 6/2013 | Daniel |
| 8,524,462 | B2 | 9/2013 | Valkirs et al. |
| 8,623,421 | B2 | 1/2014 | Daniel |
| 8,642,092 | B2 | 2/2014 | Daniel et al. |
| 8,703,206 | B2 | 4/2014 | Daniel et al. |
| 8,703,207 | B2 | 4/2014 | Daniel et al. |
| 8,709,493 | B2 | 4/2014 | Daniel et al. |
| 8,709,494 | B2 | 4/2014 | Daniel |
| 8,904,664 | B2 | 12/2014 | Pringle et al. |
| 8,932,643 | B2 | 1/2015 | Daniel et al. |
| 9,039,783 | B2 | 5/2015 | Petter-Puchner et al. |
| 9,080,184 | B2 | 7/2015 | Kharazi et al. |
| 9,084,767 | B2 | 7/2015 | Daniel et al. |
| 9,161,955 | B2 | 10/2015 | Tseng et al. |
| 9,180,145 | B2 | 11/2015 | Brown et al. |
| 9,186,382 | B2 | 11/2015 | Daniel et al. |
| 9,205,177 | B2 | 12/2015 | Schorgl et al. |
| 9,265,800 | B2 | 2/2016 | Daniel |
| 9,265,801 | B2 | 2/2016 | Daniel |
| 9,272,003 | B2 | 3/2016 | Daniel et al. |
| 9,272,005 | B2 | 3/2016 | Daniel |
| 9,415,074 | B2 | 8/2016 | Daniel et al. |
| 9,433,647 | B2 | 9/2016 | Daniel |
| 9,463,206 | B2 | 10/2016 | Koob et al. |
| 9,533,011 | B2 | 1/2017 | Daniel et al. |

(Continued)

FOREIGN PATENT DOCUMENTS

| WO | 98/08492 A1 | 3/1998 |
| WO | 2007/038686 A2 | 4/2007 |

(Continued)

OTHER PUBLICATIONS

Ward et al., Drug-Coated Balloons for Lower Extremity Interventions: Why, When, and in Whom?, American College of Cardiology, Jan. 20, 2016 (Year: 2016).*

(Continued)

*Primary Examiner* — Louise W Humphrey
*Assistant Examiner* — Srikanth Patury
(74) *Attorney, Agent, or Firm* — Merchant & Gould P.C.

(57) ABSTRACT

This document provides methods and materials for treating a mammal (e.g., a human) having one or more stenotic blood vessels. For example, amnion coated balloons that can be used in balloon angioplasty are provided.

13 Claims, No Drawings

(56) References Cited

U.S. PATENT DOCUMENTS

| | | |
|---|---|---|
| 9,555,062 B2 | 1/2017 | Pringle et al. |
| 9,572,839 B2 | 2/2017 | Daniel |
| 9,655,948 B1 | 5/2017 | Koob et al. |
| 9,662,355 B2 | 5/2017 | Koob et al. |
| 9,687,588 B2 | 6/2017 | Daniel et al. |
| 9,789,137 B2 | 10/2017 | Daniel et al. |
| 9,827,293 B2 | 11/2017 | Koob et al. |
| 10,478,531 B2 | 11/2019 | Petrucci |
| 2003/0078499 A1 | 4/2003 | Eppstein |
| 2003/0187515 A1 | 10/2003 | Hariri et al. |
| 2003/0229394 A1 | 12/2003 | Ogle et al. |
| 2003/0235563 A1 | 12/2003 | Strom et al. |
| 2003/0235580 A1 | 12/2003 | Zhang |
| 2004/0147045 A1 | 7/2004 | Nelson |
| 2005/0020500 A1 | 1/2005 | Shen et al. |
| 2005/0287223 A1 | 12/2005 | Peyman |
| 2007/0031471 A1 | 2/2007 | Peyman |
| 2007/0293872 A1 | 12/2007 | Peyman |
| 2008/0181950 A1 | 7/2008 | Bates et al. |
| 2009/0125044 A1 | 5/2009 | Lary |
| 2009/0238801 A1 | 9/2009 | Woodbury et al. |
| 2009/0270978 A1 | 10/2009 | Virkler et al. |
| 2010/0143312 A1 | 6/2010 | Hariri et al. |
| 2010/0228335 A1* | 9/2010 | Schorgl ............... A61L 31/005 623/1.15 |
| 2010/0260721 A1 | 10/2010 | McGonagie et al. |
| 2011/0307003 A1 | 12/2011 | Chambers |
| 2012/0080030 A1 | 4/2012 | Wachter |
| 2012/0171171 A1 | 7/2012 | West et al. |
| 2012/0201787 A1 | 8/2012 | Abbot et al. |
| 2012/0269785 A1 | 10/2012 | Woods et al. |
| 2013/0071358 A1 | 3/2013 | Peterson et al. |
| 2013/0238100 A1 | 9/2013 | Young |
| 2013/0243739 A1 | 9/2013 | Burt |
| 2013/0344162 A1* | 12/2013 | Morse ............... A61L 27/3695 424/582 |
| 2014/0023723 A1* | 1/2014 | Leach ............... A61L 27/3633 424/577 |
| 2014/0050788 A1* | 2/2014 | Daniel ............... A61L 26/0057 424/489 |
| 2014/0236161 A1 | 8/2014 | Brahm |
| 2014/0271776 A1 | 9/2014 | Vines et al. |
| 2015/0037436 A1 | 2/2015 | Huang et al. |
| 2015/0216910 A1 | 8/2015 | Horton et al. |
| 2015/0216912 A1 | 8/2015 | Koob |
| 2015/0231183 A1 | 8/2015 | Peterson et al. |
| 2016/0136334 A1 | 5/2016 | Schorgl et al. |
| 2016/0184479 A1 | 6/2016 | Fette |
| 2016/0193253 A1 | 7/2016 | Petrucci |
| 2016/0193254 A1 | 7/2016 | Petrucci |
| 2016/0199417 A1 | 7/2016 | Werber et al. |
| 2016/0199537 A1 | 7/2016 | Koob |
| 2016/0242905 A1* | 8/2016 | Chambers ............. A61F 2/2412 |
| 2017/0042943 A1 | 2/2017 | Namin et al. |
| 2018/0338998 A1 | 11/2018 | Petrucci |
| 2019/0083546 A1 | 3/2019 | Petrucci |
| 2019/0083547 A1 | 3/2019 | Petrucci |

FOREIGN PATENT DOCUMENTS

| | | | |
|---|---|---|---|
| WO | 2012/088396 A2 | 6/2012 | |
| WO | 2012/112410 A2 | 8/2012 | |
| WO | 2014/047067 A1 | 3/2014 | |
| WO | 2015/134936 A1 | 9/2015 | |
| WO | WO 2016/007554 * | 1/2016 | ............. C12N 5/073 |
| WO | 2016/198670 A1 | 12/2016 | |

OTHER PUBLICATIONS

Clever et al., Novel Sirolimus-Coated Balloon Catheter In Vivo Evaluation in a Porcine Coronary Model, Circ Cardiovasc Interv. 2016 (Year: 2016).*

Sobolewski et al., Wharton's Jelly as a Reservoir of Peptide Growth Factors, Placenta (2005), 26, 747-752 (Year: 2005).*

"Angioplasty or bypass surgery?," Harvard Heart Letter, Apr. 2008, 2 pages.

Alkilani et al., "Transdermal Drug Delivery: Innovative Pharmaceutical Developments Based on Disruption of the Barrier Properties of the stratum corneum," Pharmaceutics, 2015, 7: 438-470.

Anand et al., "Use of amniotic membrane graft in glaucoma shunt surgery," Opthalmic Surg Lasers Imaging, May-Jun. 2011, 42: 184-9, Abstract Only.

Brown et al., "Dermal and Transdermal Drug Delivery Systems: Current and Future Prospects," Drug Delivery, 2006, 13: 175-187.

Chen et al., "Percutaneous Thrombin Injection for Treatment of a Splenic Artery Aneurysm," Radiology case reports, 1(1):13-16, Jan. 2006.

Chen et al., "The effects of acellular amniotic membrane matrix on osteogenic differentiation and ERK1/2 signaling in human dental apical papilla cells," Biomaterials, 2012, 33(2): 455-63.

Derdeyn et al., "Collagen-Coated Acrylic Microspheres for Embolotherapy: In Vivo and In Vitro Characteristics," AJNR Am J Neuroradiol, Apr. 1997, 18:647-653.

Dhote et al., "Iontophoresis: A Potential Emergence of a Transdermal Drug Delivery System," Sci Pahrm, 2012, 80: 1-28.

Diaz-Prado et al., "Human amniotic membrane as an alternative source of stem cells for regenerative medicine," Differentiation, 2011, 81(3): 162-71.

Gerth et al., "Clinical outcomes for Conduits and Scaffolds in peripheral nerve repair," Worls J Clin Cases, Feb. 2015, 3: 141-147.

Harvard Men's Health Watch, "The crucial, controversial carotid artery Part I: The artery in health and disease," Harvard Health Publishing, Aug. 2011, 6 pages.

Hassan et al., "Neural-Differentiated Mesenchymal Stem Cells Incorporated into Muscle Stuffed Vein Scaffold Forms a Stable Living Nerve Conduit," Journal of Orthopaedic Research, Oct. 2012, 1674-1681.

International Preliminary Report on Patentability in Application No. PCT/US2015/068127, dated Jul. 11, 2017, 12 pages.

International Preliminary Report on Patentability in Application No. PCT/US2015/068136, dated Jul. 11, 2017, 11 pages.

International Preliminary Report on Patentability in International Application No. PCT/US2017/016225, dated Aug. 16, 2018.

International Search Report and Written Opinion in International Application No. PCT/US2015/68127, dated Apr. 19, 2016, 18 pages.

International Search Report and Written Opinion in International Application No. PCT/US2015/68136, dated Feb. 26, 2016, 13 pages.

International Search report and Written Opinion in International Application No. PCT/2017/016225, dated Apr. 14, 2017, 18 pages.

International Search report and Written Opinion in International Application No. PCT/US 18/38815, dated Sep. 19, 2018, 16 pages.

International Search Report & Written Opinion in International Application No. PCT/US2018/051651 dated Dec. 6, 2018, 20 pages.

Kalluri and Banga, "Transdermal Delivery of Proteins," AAPS PharmSciTech, Mar. 2011, 12: 431-441.

Khan et al., "Iontophoretic drug delivery: History and applications," Journal of Applied Pharmaceutical Science, 2011, 11-24.

Kumar and Philip, "Modified Transdermal Technologies: Breaking the Barriers of Drug Permeation via the Skin," Tropical Journal of Pharmaceutical Research, Mar. 2007, 6: 633-644.

Lei et al., "Dehydrated Human Amnion/Chorion Membrane (dHACM) Allografts as a Therapy for Orthopedic Tissue Repair," Techniques in Orthopaedics, 2017, 9 pages.

Liu, "Shunt tube implantation combining amniotic membrane transplantation and implantation of Molteno implant for glaucoma after penetrating keratoplasty," Yan Ke Xue Bao, Jun. 2000, 16: 65-72, Abstract Only.

McDonald et al., "Maintenance of human amnion epithelial cell phenotype in pulmonary surfactant," Stem Cell Research & Therapy, 2014, 5: 107.

Orth et al., "Current perspectives in stem cell research for knee cartilage repair," Stem Cells Cloning, Jan. 2014, 7: 1-17.

(56) References Cited

OTHER PUBLICATIONS

Quint et al., "Decellularized tissue-engineered blood vessel as an arterial conduit," PNAS, May 2011, 108: 9214-9219.

Robertson et al., "Angioplasty and stenting for peripheral arterial disease of the lower limbs: an overview of Cochrane Reviews (Protocol)," Cochrane Database of Systematic Reviews, Feb. 2017, 2: CD012542 (11 pages).

Sabongi et al., "Peripheral nerve regeneration with conduits: use of vein tubes," Neural Regen Res, Apr. 2015, 10: 529-533.

Vaidya et al., "An Overview of Embolic Agents," Seminars in Interventional Radiology, 2008, 25: 204-215.

Wilshaw et al., "Production of an acellular amniotic membrane matrix for use in tissue engineering," Tissue Eng., 2006, 12(8): 2117-29.

Zhan et al., "Nanofiber scaffolds facilitate functional regeneration of peripheral nerve injury," Nanomedicine, 2013, 9: 305-315.

\* cited by examiner

METHODS AND MATERIALS FOR TREATING BLOOD VESSELS

CLAIM OF PRIORITY

This application is a continuation of U.S. Utility Application No. 15/708,406 filed Sep. 19, 2017, now U.S. Pat. No. 10,478,531, which claims priority to U.S. Provisional Application Ser. No. 62/523,366, filed on Jun. 22, 2017, the entire contents of which are hereby incorporated by reference.

BACKGROUND

1. Technical Field

This document relates to methods and materials for treating a mammal (e.g., a human) having one or more stenotic blood vessels. For example, amnion coated balloons provided herein can be used in balloon angioplasty.

2. Background Information

Angioplasty is frequently used to treat heart disease and peripheral artery disease (PAD). Heart disease is the leading cause of death for both men and women, and PAD affects at least 8 to 12 million Americans with prevalence increasing with age (CDC, *Heart Disease Facts*. Available online at cdc.gov/heartdisease/facts.htm). Each year, more than 1 million patients in the United States have angioplasty (American Heart Association. *Heart Disease and Stroke Statistics*-2007 Update. Dallas, Tex.: American Heart Association; 2007), but up to one-quarter of people who have angioplasty must have it repeated, or, in the case of heart disease, have bypass surgery within a few years (Harvard Health Publications, "Angioplasty or bypass surgery?" *Harvard Heart Letter* April 2008).

SUMMARY

This document provides methods and materials for treating a mammal (e.g., a human) having one or more stenotic blood vessels. For example, amnion coated balloons provided herein (e.g., an angioplasty balloon coated with an amnion tissue preparation) can be used in balloon angioplasty. In some cases, amnion coated balloons provided herein can be used to treat a mammal having one or more stenotic blood vessels. Typically, a stent is placed into a blood vessel following balloon angioplasty to decrease recoil (e.g., restenosis) of the blood vessel. In some cases, amnion coated balloons provided herein can be used in stent-less balloon angioplasty (e.g., a balloon angioplasty in which a stent is not implanted).

In general, one aspect of this document features an angioplasty balloon (e.g., a balloon of a balloon catheter) having a coating including an amnion tissue preparation. The amnion tissue preparation can have viable cells or the amnion tissue preparation can lack viable cells. The amnion tissue preparation can be a dried amnion tissue preparation. A dried amnion tissue preparation can have a water content less than about 8 percent. A dried amnion tissue preparation can have a particle size ranging from about 0.1 µm to about 25 µm. The amnion tissue preparation can be the sole active ingredient on the amnion coated balloon or the amnion coated balloon also can be coated with one or more therapeutic agents. The angioplasty balloon catheter can be a stent-less angioplasty balloon catheter.

In another aspect, this document features methods for treating stenotic blood vessel in a mammal. The methods can include, or consist essentially of, inserting an angioplasty balloon into an obstructed blood vessel, where the angioplasty balloon has a coating including an amnion tissue preparation, and inflating the amnion coated balloon to perform angioplasty in the obstructed vessel. In some cases, one or more symptoms associated with said stenotic blood vessel can be reduced. When the stenotic blood vessel is a peripheral artery, the symptom can be claudication, cramps, tingling, pain, numbness, wounds, reduced body temperature, and/or poor nail growth, in the arms and/or legs. When the stenotic blood vessel is a stenotic coronary artery, the symptom can be stroke, heart attack, chest pain, shortness of breath, sweating, nausea, dizziness or light-headedness, palpitations, and/or arrhythmias. When the stenotic blood vessel is a stenotic carotid artery, the symptom can be weakness, confusion, difficulty speaking, dizziness, difficulty walking, difficulty standing, blurred vision, numbness, severe headache, and/or losing consciousness. When the stenotic blood vessel is a stenotic renal artery stenosis, the symptom can be decreased kidney blood flow, and/or chronic kidney disease. In some cases, the obstructed blood vessel is widened. The obstructed blood vessel can be widened to be about 20% to about 100% open. In some cases, the obstruction in said obstructed blood vessel is reduced. The obstruction can be reduced by about 20% volume to about 100% volume. In some cases, the blood flow in the obstructed blood vessel can be increased. The blood flow can be increased by about 20% to about 100%. The blood flow can be increased to between about 50 cm/s and about 250 cm/s. The mammal can be a human. The amnion coated balloon can be inflated to from about 5 atmospheres (atm) to about 35 atm of pressure. The amnion coated balloon can be inflated to less than about 10 atm of pressure. The angioplasty can have less than about 50% recoil. The angioplasty balloon can be inserted through a percutaneous puncture in the arm or groin. The obstruction can include an atherosclerotic plaque (e.g., a calcified atherosclerotic plaque). The method also can include (e.g., prior to said angioplasty) performing atherectomy in the obstructed vessel. The method can be a stent-less balloon angioplasty.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides amnion coated balloons (e.g., angioplasty balloons coated with an amnion tissue preparation), as well as methods and materials for making and using amnion coated balloons. For example, amnion coated balloons provided herein (e.g., an angioplasty balloon coated with an amnion tissue preparation) can be used in balloon angioplasty. In some cases, amnion coated balloons provided herein can be used to treat a mammal (e.g., a human) having one or more stenotic blood vessels. For example, an amnion coated balloon can be used in balloon angioplasty to treat a mammal having one or more (e.g., two, three, four, or more) stenotic blood vessels. In some cases, amnion coated balloons provided herein can be used in balloon angioplasty to reduce the symptoms associated with a stenotic blood vessel, widen a stenotic blood vessel, reduce or remove an obstruction from a stenotic blood vessel, and/or increase blood flow in a stenotic blood vessel. In some cases, a balloon catheter having an amnion coated balloon can be used to deliver an amnion tissue preparation to a stenotic blood vessel (e.g., to promote healing in the stenotic blood vessel).

An amnion coated balloon provided herein can be coated with an amnion tissue preparation (e.g., human amnion tissue preparation). In some cases, an amnion coated balloon can be completely coated with an amnion tissue preparation. In some cases, an amnion coated balloon can be partially coated with an amnion tissue preparation. The term "amnion tissue preparation" as used herein refers to a preparation of amnion tissue or amnion material. In some cases, an amnion tissue preparation can be a liquid preparation (e.g., solution or suspension) that is prepared from a dried amnion tissue preparation. The term "dried amnion tissue preparation" as used herein refers to a preparation of amnion tissue or amnion material that is dried to have a water content that is less than about 8 percent (e.g., less than about 7 percent, less than about 6 percent, less than about 5 percent, less than about 4 percent, less than about 3 percent, less than about 2 percent, or less than about 1 percent). In some cases, a dried amnion tissue preparation can have a water content that is between about 0.1 percent and about 8 percent (e.g., between about 0.5 percent and about 8 percent, between about 1 percent and about 8 percent, between about 0.1 percent and about 5 percent, between about 0.1 percent and about 4 percent, between about 0.1 percent and about 3 percent, between about 0.5 percent and about 5 percent, or between about 1 percent and about 4 percent).

An amnion tissue preparation can be dried using any appropriate technique such as micronization, vacuum drying, spray drying, freeze drying, or combinations thereof. In some cases, an amnion tissue preparation can be dried as described elsewhere (e.g., U.S. Pat. No. 5,656,498). A dried amnion tissue preparation can have any appropriate particle size. For example, a dried amnion tissue preparation can have a particle size ranging from about 0.1 µm to about 25 µm (e.g., from about 0.5 µm to about 25 µm, from about 0.75 µm to about 25 µm, from about 1 µm to about 25 µm, from about 0.1 µm to about 15 µm, from about 0.1 µm to about 10 µm, from about 0.1 µm to about 7.5 µm, from about 0.1 µm to about 5 µm, from about 0.75 µm to about 7.5 µm, or from about 1 µm to about 5 µm).

An amnion tissue preparation or a dried amnion tissue preparation can contain viable cells, non-viable cells, or a combination thereof. For example, an amnion tissue preparation or a dried amnion tissue preparation can be a preparation of amnion tissue or amnion material having viable cells. In some cases, an amnion tissue preparation can be a solution or suspension of amnion tissue or amnion material having viable cells.

In some cases, an amnion tissue preparation or a dried amnion tissue preparation can be a preparation of amnion tissue or amnion material where all the cells were removed, killed, or lysed such that the amnion tissue preparation or the dried amnion tissue preparation lacks viable cells. In some cases, an amnion tissue preparation or a dried amnion tissue preparation can be a preparation of amnion tissue or amnion material that was exposed to one or more physical and/or chemical treatments that killed, fixed, or lysed the cells of the amnion tissue or amnion material such that the amnion tissue preparation or the dried amnion tissue preparation lacks viable cells. For example, temperature (e.g., rapid freezing or rapid freezing-thawing), force and pressure, and/or electrical disruption can be used to kill or lyse cells within amnion tissue or amnion material to produce an amnion tissue preparation or a dried amnion tissue preparation that lacks viable cells.

In some cases, amnion tissue or amnion material can be obtained and then treated in a manner designed to lyse all the cells within the amnion tissue or amnion material. In these cases, the resulting material (e.g., matrix material and cellular remnants from lysed cells) can be used as an amnion tissue preparation that lacks viable cells or dried to form a dried amnion tissue preparation that lacks viable cells.

In some cases, an amnion tissue preparation or a dried amnion tissue preparation can be prepared from human amnion tissue. For example, human amnion tissue can be harvested, processed to maintain cell viability with or without removing blood, and used as an amnion tissue preparation or dried to form a dried amnion tissue preparation.

In some cases, human amnion tissue can be processed to remove blood prior to being used as an amnion tissue preparation or prior to being dried to form a dried amnion tissue preparation. In some cases, human amnion tissue can be processed without removing cells or blood prior to forming an amnion tissue preparation or a dried amnion tissue preparation.

An example of an amnion tissue preparation includes, without limitation, a human amnion tissue preparation that includes viable cells. In some cases, an amnion tissue preparation can be obtained from MiMedX® or a tissue bank (e.g., a human tissue bank).

In some cases, an amnion tissue preparation also can include one or more therapeutic agents (e.g., a therapeutic agent that can be used to treat calcium deposits), one or more immunosuppressant agents (e.g., corticosteroids such as glucocorticoids), one or more anti-inflammatory agents (e.g., non-steroidal anti-inflammatory drugs, dexamethasone or other type of glucocorticoid steroids), one or more growth factors (e.g., vascular endothelial growth factor (VEGF), epithelial growth factor (EGF), fibroblast growth factor-2 (FGF2), or stem cell factor (SCF)), and/or one or more antimicrobial agents (e.g., antibiotics such as kanamycin, neomycin, streptomycin, or gentamicin, or an antifungal agent).

In some cases, an amnion coated balloon provided herein can be coated with an amnion tissue preparation (e.g., human amnion tissue preparation) as the sole active ingredient.

In some cases, an amnion coated balloon provided herein can be coated with an amnion tissue preparation (e.g., human amnion tissue preparation) and another therapeutic agent. Examples of therapeutic agents that can be used to coat and amnion coated balloon provided herein include, without limitation, immunosuppressive drugs (e.g., rapamycin and everolimus) and antiproliferative drugs (e.g., paclitaxel).

An amnion tissue preparation can be coated onto a balloon to produce an amnion coated balloon provided herein using any appropriate method. For example, in cases where an amnion tissue preparation is a liquid preparation (e.g., solution or suspension), a balloon can be dipped into or sprayed with the liquid preparation.

This document also provides methods for using amnion coated balloons provided herein. In some cases, amnion coated balloons provided herein can be used to treat a mammal (e.g., a human) having one or more stenotic blood vessels. For example, an amnion coated balloon can be used for treating a mammal (e.g., a human) having one or more stenotic blood vessels. In some cases, an amnion coated balloon can be used in balloon angioplasty to reduce the symptoms associated with a stenotic blood vessel, widen a stenotic blood vessel, reduce or remove an obstruction from a stenotic blood vessel, and/or increase blood flow in a stenotic blood vessel. In some cases, an amnion coated balloon can be used in balloon angioplasty to deliver an amnion tissue preparation (e.g., an effective amount of an amnion tissue preparation described herein) to a stenotic blood vessel (e.g., to promote healing in the stenotic blood vessel). Effective amounts of amnion tissue preparations described herein can be determined by a physician, taking into account various factors such as overall health status, body weight, sex, diet, time and route of administration, other medications, and any other relevant clinical factors. As used herein, an "effective amount" or "therapeutically effective amount" of a composition provided herein is the amount that is sufficient to provide a beneficial effect to the subject to which the composition or preparations are delivered. The effective amount can be the amount effective to achieve an improvement or elimination of one or more symptoms (e.g., symptoms associated with a stenotic blood vessel), widen a stenotic blood vessel, reduce or remove an obstruction from a stenotic blood vessel, and/or increase blood flow in a stenotic blood vessel.

In some cases, amnion coated balloons provided herein can be used in balloon angioplasty (e.g., coronary angioplasty, peripheral angioplasty, carotid angioplasty, venous angioplasty, femoral angioplasty, popliteal angioplasty, and tibial angioplasty). In some cases, amnion coated balloons provided herein can be used in stent-less balloon angioplasty (e.g., a balloon angioplasty in which a stent is not implanted). In some cases, amnion coated balloons provided herein can be used in balloon angioplasty that includes implanting stent. In cases where angioplasty with an amnion coated balloon includes implanting a stent, the stent can be implanted during the angioplasty procedure. For example, the stent can be provided on the same balloon catheter having an amnion coated balloon provided herein. In cases where angioplasty with an amnion coated balloon includes implanting a stent, the stent can be implanted after the angioplasty procedure. For example, the stent can be provided independently of an amnion coated balloon provided herein. In cases where angioplasty with an amnion coated balloon includes implanting a stent, the stent can be any appropriate stent.

A stent can be made of any appropriate material (e.g., metals (such as nickel (e.g., nickel titanium), iron, magnesium, zinc, and/or alloys thereof) and/or polymers (such as poly(L-lactide) (PLLA); poly-D, L-lactide (PDLLA); tyrosine poly carbonate, and/or poly(anhydride-esters)-salicylates)). Examples of types of stents include, without limitation, bare stents, drug-eluting stents, bioabsorbable stents, coated stents, and combinations thereof. In cases where angioplasty with an amnion coated balloon includes implanting a drug-elutin stent, the stent can elute any appropriate drug (e.g., immunosuppressive drugs (such as rapamycin and everolimus) and antiproliferative drugs (such as paclitaxel)). In cases where angioplasty with an amnion coated balloon includes implanting a coated stent, the stent can be coated (e.g., completely coated or partially coated) with an amnion preparation described herein.

Methods of using amnion coated balloons provided herein can include inserting an amnion coated balloon provided herein into a stenotic blood vessel and inflating the amnion coated balloon. For example, an amnion coated balloon provided herein can be inflated to a pressure of from about 4 atm to about 35 atm (e.g., from about 4 atm to about 30 atm, from about 4 atm to about 25 atm, from about 4 atm to about 20 atm, from about 4 atm to about 15 atm, from about 4 atm to about 10 atm, from about 6 atm to about 35 atm, from about 8 atm to about 35 atm, from about 10 atm to about 35 atm, from about 15 atm to about 35 atm, from about 20 atm to about 35 atm, from about 5 atm to about 30 atm, from about 6 atm to about 25 atm, from about 8 atm to about 23 atm, or from about 10 atm to about 20 atm). In some cases, an amnion coated balloon can be inflated at low pressure (e.g., lower pressure than is typically used with balloon angioplasty that includes implanting stent). For example, an amnion coated balloon provided herein inflated at low pressure can be inflated to a pressure of less than about 10 atm (e.g., less than about 9 atm, less than about 8 atm, less than about 7 atm, less than about 6 atm, or less than about 5 atm). Methods of using amnion coated balloons provided herein also can include deflating and removing the amnion coated balloons.

An amnion coated balloon provided herein can be inserted into the stenotic blood vessel using any appropriate technique. For example, an amnion coated balloon can be inserted through a percutaneous puncture in the arm or groin. In some cases, methods of using amnion coated balloons provided herein can include using a guidewire to guide an amnion coated balloon to a stenotic blood vessel. In some cases, methods of using amnion coated balloons provided herein can include using optical imaging (e.g., X-ray, fluoroscopic guidance, and/or radiopaque contrast dye) to guide an amnion coated balloon to a stenotic blood vessel.

In some cases, a mammal can be identified as having one or more stenotic blood vessels using any appropriate technique. Examples of techniques that can be used to identify a mammal as having one or more stenotic blood vessels include, without limitation, angiography (e.g., coronary angiography), microphotography, stress testing, ultrasound (e.g., Doppler ultrasound and intravascular ultrasound), coronary calcium scoring (e.g., by CT), carotid measurement (e.g., carotid intimal media thickness (IMT) measurement by ultrasound), physiologic measurement (e.g., lipoprotein subclass analysis, HbA1c, hs-CRP, and homocysteine), and/or nuclear imaging techniques (e.g., PET and SPECT).

A stenotic blood vessel can be in any appropriate location of the body. Examples of body locations that can have stenotic blood vessels include, without limitation, the legs, the neck, the heart, the kidneys, the aorta, the chest, and the abdomen.

When a stenotic blood vessel is an obstructed blood vessel, the obstruction can be any appropriate type of obstruction. Examples of obstructions that can narrow a blood vessel include, without limitation, calcification (e.g., calcium deposits that accumulate and/or crystallize in soft tissues such as arteries), and plaques (e.g., atherosclerotic plaques such as atheromatous plaques). In some cases, plaques can include calcification (e.g., a calcified plaque). For example, a human having stenosis can have calcification in a carotid artery.

Any type of mammal having one or more stenotic blood vessels can be treated as described herein. Examples of mammals that can be treated with an amnion coated balloon provided herein include, without limitation, non-human primates (e.g., monkeys), dogs, cats, horses, cows, pigs, sheep, rabbits, mice, and rats. For example, humans having one or more stenotic blood vessels can be treated with an amnion coated balloon provided herein.

When treating a mammal (e.g., a human) having one or more stenotic blood vessels, any appropriate blood vessel (e.g., an artery or a vein) can be narrowed and/or obstructed. In cases where a stenotic blood vessel is an artery, the artery can be a peripheral artery (e.g., a leg artery such as a popliteal artery, a tibial artery (e.g., a posterior or anterior tibial artery), a peroneal artery, a plantar artery (e.g., a lateral, medial, or deep plantar artery), or a dorsalis pedis artery), a coronary artery (e.g., a carotid artery, a distal left main coronary artery (LMCA), a left circumflex artery (LCX), or a left anterior descending (LAD) artery), or a renal artery. In cases where a stenotic blood vessel is a vein, the vein can be a subclavian vein. For example, a human having a stenotic carotid artery can be treated using an amnion coated balloon provided herein in an angioplasty procedure described herein (e.g., a stent-less angioplasty procedure).

In some cases, a mammal (e.g., a human) having one or more stenotic blood vessels can have a condition associated with one or more stenotic blood vessels. The condition associated with one or more stenotic blood vessels can be any appropriate condition. Examples of conditions that can include a stenotic (e.g., narrowed and/or obstructed) blood vessel include, without limitation, heart disease, cardiovascular disease, arteriosclerosis (e.g., atherosclerosis), peripheral artery disease (PAD; e.g., PAD associated with diabetes), renal vascular hypertension, carotid artery disease, and coronary artery disease (CAD). For example, a human having atherosclerosis can be treated using an amnion coated balloon provided herein in an angioplasty procedure described herein (e.g., a stent-less angioplasty procedure). For example, a human having CAD can be treated using an amnion coated balloon provided herein in an angioplasty procedure described herein (e.g., a stent-less angioplasty procedure).

In some cases, the methods and materials provided herein can be used to reduce the symptoms associated with one or more stenotic blood vessels. In some cases, a balloon catheter having an amnion coated balloon can be used to reduce one or more (e.g., two, three, four, or more) symptoms associated with stenotic blood vessel. It will be appreciated that symptoms associated with stenosis will differ according to which blood vessel is stenotic and according to which organ(s) the stenotic blood vessel supplies blood. For example, symptoms associated with a stenotic coronary artery can include, without limitation, cardiovascular disorders (e.g., stroke or heart attack), chest pain (e.g., angina), shortness of breath, sweating, nausea, dizziness or lightheadedness, palpitations, and arrhythmias. For example, symptoms associated with a stenotic carotid artery can include, without limitation, weakness, confusion, difficulty speaking, dizziness, difficulty walking, difficulty standing, blurred vision, numbness (e.g., of the face, arms, and/or legs), severe headache, and losing consciousness. For example, symptoms associated with a stenotic peripheral artery can include, without limitation, claudication, cramps, tingling, pain, numbness, wounds, reduced body temperature, and poor nail growth in the arms and/or legs. For example, symptoms associated with a stenotic renal artery can include, without limitation, decreased kidney blood flow, and chronic kidney disease. In some cases, a balloon catheter having an amnion coated balloon can be used to eliminate one or more symptoms associated with a stenotic blood vessel. For example, a human having one or more stenotic blood vessels can be treated using an amnion coated balloon provided herein in an angioplasty procedure described herein (e.g., a stent-less angioplasty procedure) to reduce or eliminate claudication, cramps, tingling, pain, numbness, wounds, reduced body temperature, and/or poor nail growth in the hands and/or feet. For example, a human having one or more stenotic blood vessels can be treated using an amnion coated balloon provided herein in an angioplasty procedure described herein (e.g., a stent-less angioplasty procedure) to reduce or eliminate chest pain.

In some cases, the methods and materials provided herein can be used to widen (e.g., re-open) a stenotic blood vessel. In some cases, an amnion coated balloon (e.g., a balloon catheter having an amnion coated balloon) described herein can be inflated within a stenotic blood vessel to widen the blood vessel. For example, a human having one or more stenotic blood vessels can be treated using an amnion coated balloon provided herein in an angioplasty procedure described herein (e.g., a stent-less angioplasty procedure) to widen a stenotic blood vessel. In some cases, the methods provided herein can include widening a stenotic blood vessel to be from about 20% to about 100% open (e.g., about 25% to about 95%, about 30% to about 90%, about 50% to about 80%, about 60% to about 75%, about 20% to about 80%, about 20% to about 50%, about 25% to about 50%, about 30% to about 100%, about 40% to about 100%, about 50% to about 100%, or about 75% to about 100% open). For example, an amnion coated balloon provided herein can be inflated within a stenotic blood vessel to completely (e.g., 100%) open the blood vessel. In some cases, the methods provided herein (e.g., following the angioplasty) can have less than about 50% (e.g., less than about 45%, less than about 40%, less than about 30%, less than about 25%, less than about 20%, less than about 15%, less than about 10%, or less than about 5%) recoil.

In some cases, the methods and materials provided herein can be used to reduce or remove an obstruction from a stenotic blood vessel. In some cases, an amnion coated balloon (e.g., a balloon catheter having an amnion coated balloon) described herein can be inflated within a stenotic blood vessel to reduce or remove an obstruction from the blood vessel. For example, a human having one or more stenotic blood vessels can be treated using an amnion coated balloon provided herein in an angioplasty procedure described herein (e.g., a stent-less angioplasty procedure) to reduce or remove an obstruction from a stenotic blood vessel. In some cases, the methods provided herein can include reducing the size of an obstruction in a blood vessel by from about 20% volume to about 100% volume (e.g., about 25% to about 95%, about 30% to about 90%, about 50% to about 80%, about 60% to about 75%, about 20% to about 80%, about 20% to about 50%, about 25% to about 50%, about 30% to about 100%, about 40% to about 100%, about 50% to about 100%, or about 75% to about 100% volume). For example, an amnion coated balloon provided herein can be inflated within a stenotic blood vessel to completely remove (e.g., reduce by 100%) an obstruction in a blood vessel.

In some cases, the methods and materials provided herein can be used to increase blood flow in a blood vessel. In some cases, an amnion coated balloon (e.g., a balloon catheter having an amnion coated balloon) described herein can be inflated within a stenotic blood vessel to increase blood flow in the blood vessel. For example, a human having one or more stenotic blood vessels can be treated using an amnion coated balloon provided herein in an angioplasty procedure described herein (e.g., a stent-less angioplasty procedure) to increase blood flow in a blood vessel. In some cases, the methods provided herein can include increasing blood flow in a blood vessel by from about 20% to about 100% (e.g., about 25% to about 95%, about 30% to about 90%, about 50% to about 80%, about 60% to about 75%, about 20% to about 80%, about 20% to about 50%, about 25% to about 50%, about 30% to about 100%, about 40% to about 100%, about 50% to about 100%, or about 75% to about 100%). In some cases, the methods provided herein can be used to increase blood flow in an artery to between about 50 cm/s and about 250 cm/s (e.g., between about 55 cm/s and about 250 cm/s, between about 60 cm/s and about 250 cm/s, between about 75 cm/s and about 250 cm/s, between about 100 cm/s and about 250 cm/s, between about 50 cm/s and about 225 cm/s, between about 50 cm/s and about 200 cm/s, between about 50 cm/s and about 175 cm/s, between about 50 cm/s and about 150 cm/s, between about 65 cm/s and about 225 cm/s, between about 75 cm/s and about 200 cm/s, or between about 100 cm/s and about 150 cm/s). For example, an amnion coated balloon provided herein can be inflated within a stenotic artery to restore a normal blood flow.

In some cases, the methods and materials provided herein can be used to deliver an amnion tissue preparation to a stenotic blood vessel. In some cases, an amnion coated balloon (e.g., a balloon catheter having an amnion coated balloon) described herein can be inflated within a stenotic blood vessel to reduce or remove an obstruction from the blood vessel. For example, an amnion coated balloon (e.g., a balloon catheter having an amnion coated balloon) described herein can be inflated within a stenotic blood vessel to deliver an amnion tissue preparation to a stenotic blood vessel. In some cases, the methods provided herein can include delivering, to mammal (e.g., a human), an amnion tissue preparation made with from about 0.01 mg to about 10 g (e.g., from about 0.01 mg to about 10 g, from about 0.1 mg to about 10 g, from about 1 mg to about 10 g, from about 10 mg to about 10 g, from about 100 mg to about 10 g, from about 1 g to about 10 g, from about 0.01 mg to about 5 g, from about 0.01 mg to about 1 g, from about 0.01 mg to about 100 mg, from about 10 mg to about 5 g, from about 100 mg to about 1 g, or from about 1 g to about 5 g) of amnion tissue per kg body weight of the subject being treated.

Methods for using amnion coated balloons provided herein (e.g., for treating a mammal (e.g., a human) having one or more stenotic blood vessels can be used as a combination therapy with one or more additional agents/therapies used to treat heart disease (e.g., heart disease involving one or more stenotic blood vessels). For example, a combination therapy used to treat stenotic blood vessels can include angioplasty with an amnion coated balloon provided herein and administering to the mammal one or more agents for treating stenotic blood vessels such as beta blockers (e.g., metoprolol, atenolol, and bisoprolol), angiotensin II receptor blockers (e.g., losartan, valsartan, and olmesartan), statins (e.g., atorvastatin, lovastatin, simvastatin), and blood thinners (e.g., anticoagulants such as heparin or warfarin, and antiplatelet drugs such as aspirin. In cases where a stenotic blood vessel includes calcification (e.g., a calcified plaque), the methods provided herein can include one or more agents and/or therapies to treat calcification. Examples of agents that can be used to treat calcification include, without limitation, vitamin K (e.g., vitamin K2), and vitamin D (e.g., if vitamin K is normal). Examples of therapies that can be used to treat calcification include, without limitation, atherectomy (e.g., orbital, rotational, laser, or directional atherectomy). In cases where amnion coated balloons described herein are used in combination with one or more agents/therapies for treating stenotic blood vessels, the one or more agents/therapies for treating stenotic blood vessels can be administered/performed at the same time or independently. For example, angioplasty with an amnion coated balloon provided herein can be performed first, and the one or more agents/therapies for treating stenotic blood vessels can be administered second, or vice versa.

The invention will be further described in the following examples, which do not limit the scope of the invention described in the claims.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A balloon catheter kit comprising:
   a stentless balloon catheter coated with a coating consisting of a dried amnion tissue and optionally one or more agents selected from the group consisting of: agents used to treat calcium deposits, immunosuppressive agents, antimicrobial agents, antiproliferatives, and combinations thereof; and
   a stent capable of being implanted independently of the balloon.

2. The balloon catheter kit of claim 1, wherein said amnion tissue is the sole active agent in said coating.

3. The balloon catheter kit of claim 1, wherein said amnion tissue has viable cells.

4. The balloon catheter kit of claim 1, wherein said amnion tissue lacks viable cells.

5. The balloon catheter kit of claim 1, wherein said stentless balloon catheter is completely coated with said coating.

6. The balloon catheter kit of claim 1, wherein said stentless balloon catheter is partially coated with said coating.

7. A method of treating a blood vessel in a mammal comprising:
   inserting the stentless balloon catheter of claim 1 into said blood vessel; and
   inflating said stentless balloon catheter within said blood vessel.

8. The method of claim 7, wherein the method further comprises performing atherectomy in said vessel prior to inserting said stentless balloon catheter.

9. The method of claim 7, wherein said blood vessel is a stenotic blood vessel.

10. The method of claim 7, wherein said treating comprises performing balloon angioplasty on said mammal.

11. The method of claim 10, wherein said angioplasty is a stentless angioplasty.

12. A method of treating heart disease or peripheral artery disease (PAD) in a mammal comprising:
- inserting the stentless balloon catheter of claim 1 into a blood vessel of a mammal; and
- inflating said stentless balloon catheter within said blood vessel.

13. The balloon catheter kit of claim 1, wherein the stent comprises the coating.

\* \* \* \* \*